United States Patent
Joshi et al.

(10) Patent No.: US 6,989,465 B1
(45) Date of Patent: Jan. 24, 2006

(54) S-(−)-1-{4-[2-(ALLYLOXY)-ETHYL] PHENOXY}-3-ISOPROPYLAMINO PROPAN-2-OL, PROCESS FOR PREPARATION THEREOF AND PROCESS FOR PREPARATION OF S-(−)BETAXOLO

(75) Inventors: Ramesh Anna Joshi, Maharashtra (IN); Muthukrishnan Murugan, Maharashtra (IN); Dinesh Rämesh Garud, Maharashtra (IN); Sanjay Pandurang Borikar, Maharashtra (IN); Mukund Keshav Gurjar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/978,898

(22) Filed: Nov. 1, 2004

(51) Int. Cl.
*C07C 213/00* (2006.01)
(52) U.S. Cl. ...................... 564/349; 564/304
(58) Field of Classification Search ................ 564/349, 564/304
See application file for complete search history.

(56) References Cited

U.S. PATENT DOCUMENTS 4,760,182 A * 7/1988 Ippolito et al. ............. 564/349

* cited by examiner

*Primary Examiner*—Samuel Barts
(74) *Attorney, Agent, or Firm*—Morgan & Finnegan, LLP

(57) ABSTRACT

The present invention relates to a novel compound S-(−)-1-{4-[2-(allyloxy)-ethyl] phenoxy}-3-isopropylamino propan-2-ol of formula 1 and to a process for the preparation thereof. More particularly the present invention relates to a process for preparing S-(−)-1-{4-[2-(allyloxy)-ethyl]phenoxy}-3-isopropylamino propan-2-ol of formula 1 by selective allylation of p-hydroxy phenyl ethanol. The present invention also relates to a process for conversion thereof to S-(−)-betaxolol of formula 2

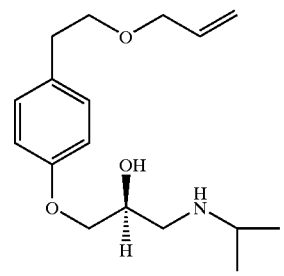

Formula (1)

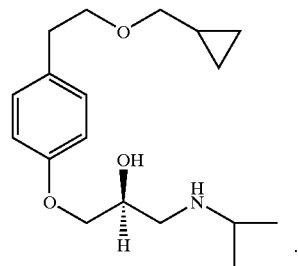

Formula (2)

14 Claims, No Drawings

S-(−)-1-{4-[2-(ALLYLOXY)-ETHYL] PHENOXY}-3-ISOPROPYLAMINO PROPAN-2-OL, PROCESS FOR PREPARATION THEREOF AND PROCESS FOR PREPARATION OF S-(−)BETAXOLO

FIELD OF THE INVENTION

The present invention relates to a novel compound S-(−)-1-{4-[2-(allyloxy)-ethyl] phenoxy}-3-isopropylamino propan-2-ol of formula 1 and to a process for the preparation thereof. More particularly the present invention relates to a process for preparing S-(−)-1-{4-[2-(allyloxy)-ethyl]phenoxy}-3-isopropylamino propan-2-ol of formula 1 by selective allylation of p-hydroxy phenyl ethanol. The present invention also relates to a process for conversion thereof to S-(−)-betaxolol of formula 2.

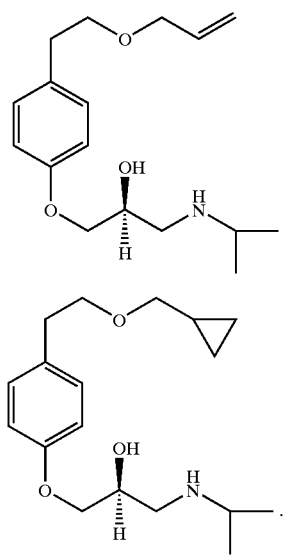

Formula (1)

Formula (2)

BACKGROUND OF THE INVENTION

Racemic betaxolol is a β-adrenoreceptor antagonist with a pharmacological and pharmacokinetic profile for the treatment of chronic cardiovascular diseases like glaucoma. The disease glaucoma is characterized by the progressive damage to the optic nerve caused by the increased pressure within the eye. Glaucoma is a serious disease of the eye, which may lead to the loss of peripheral vision and if untreated total blindness.

β-adrenoreceptor antagonist (β-blockers) are popularly used to lower intraoccular tension, other conditions of increased intraoccular pressure and management of essential hypertension. The principle effect of β-adrenoreceptor blocker is to reduce cardiac activity by diminishing or preventing β-adrenoreceptor stimulation i.e. by reducing the rate and force of contraction of the heart.

Betaxolol belongs to aryloxypropanolamine class of drugs having a specific action on the cardiovascular receptor sites. Most of the drugs in this series contain one chiral carbon centre but generally administered as racemates. Pharmacological studies have shown that an organism often reacts in a different way when it interacts with each enantiomer of the same molecule. This has promoted the growth of both the switch from the use of racemic drug to single enantiomer drug and innovation the manufacturing processes to make enantiomerically pure molecules with low cost. Although most of the β-blockers are sold as racemates, only S-isomer is associated with β-blocking activity, while the R-isomer is usually responsible for side effects. (Hussian S. S. et al, Toxiocol, 1989, 12)

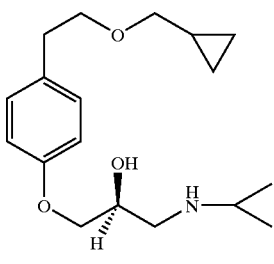

Formula (2)

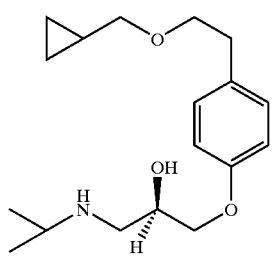

Formula (3)

The pharmacological characteristics of S-(−)-Betaxolol (Levobetaxolol) of formula 2, a single active isomer of betaxolol exhibited a higher affinity at cloned human β-1 than at β-2 receptors while R-(+)-Betaxolol (Dextrobetaxolol) of formula 3 was much weaker at both receptors. Levobetaxolol was 89-times β-1 selective vs. β-2. Levobetaxolol is more potent than Dextrobetaxolol at inhibiting isoproterenol induced CAMP production in human nonpigmented ciliary epithelial cells and exhibited a micro molar affinity for L-type $Ca^{2+}$ channels. In conclusion, levobetaxolol is a potent, high affinity and β-1 selective 10P lowering β1 adrenoreceptor antagonist.

The processes employed for the preparation of betaxolol involved protecting the phenol functional group so that the alcohol functionality can be alkylated. The resulting protection and deprotection steps extend the length of synthesis.

Manoury et al., (U.S. Pat. No. 4,252,984) describe preparation of betaxolol by the benzylation of the phenolic alcohol of 4-hydroxyphenethanoic acid. The ester group is then reduced to alcohol 2-(4-benzyloxyphenyl)ethanol which is then condensed with cyclopropyl methyl halide to yield cyclopropyl methyl2-(4-benzyloxyphenyl) ether. This is then debenzylated and treated with epichlorohydrin to yield the compound, which on treatment with isopropylamine gives the betaxolol.

U.S. Pat. No. 4,760,182 by Ippolito et al., teaches the conversion of 4-hydroxyphenethanol to a phenoxide anion with a base and then reaction with epichlorohydrin to yield 1-(4-(2-hydroxyethyl)phenoxy)2,3-epoxypropane.

Wang et al., (U.S. Pat. No. 5,731,463) describe selective alkylation of 4-hydroxy phenethanol via an oxygen dianion to produce an intermediate, which on reaction with epichlorohydrin and subsequent addition of isopropylamine produces betaxolol.

Synthesis of S-(−)-betaxolol of formula 2 has been reported by alkylation of phenol derivative of formula 10 with S-(−)-2-phenyl-3-isopropyl-5-hydroxymethyl oxazolidinyl tosylate of formula 11 followed by the acid catalyzed hydrolysis (Philippe M. Manoury; Jean L. Binet; Jean Rousseau; *J. Med. Chem.* 1987,30,1003–1011.).

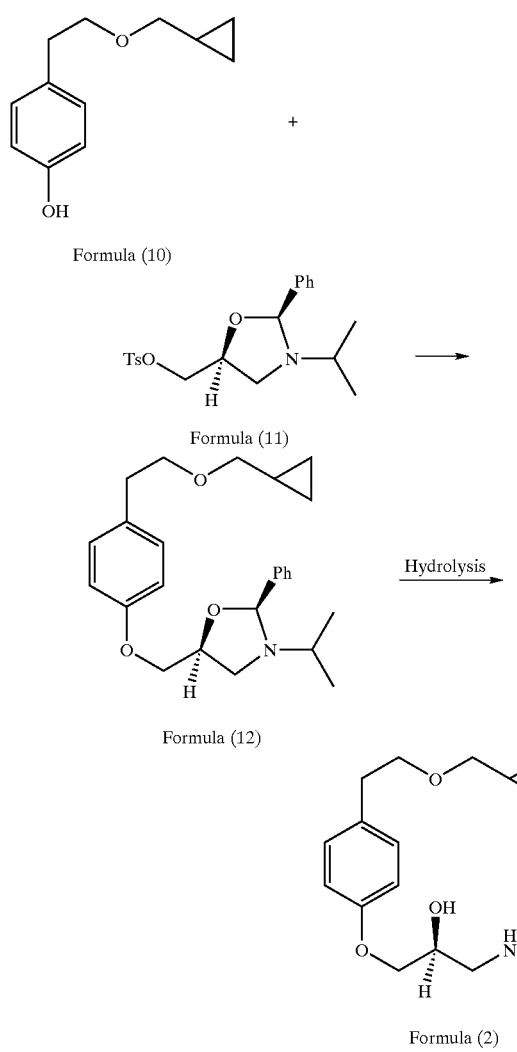

The enantiomers of betaxolol have been prepared via lipase catalyzed kinetic resolution of racemic drug (Giuseppe Di Bono; Antonio Scilimuti; *Synthesis,* 699, June1995). The racemic drug on treatment with acetic anhydride afforded N,O-bisacetylated derivative which was hydrolyzed enantio-selectively using PPL or lipase K-10. Alternatively trans esterification reaction was performed using vinyl acetate as the acyl doner on the key intermediate 1-chloro-3-[4(2-cyclopropylmethoxy)ethyl]-phenoxy propan-2-ol.

Drawbacks:

The asymmetric synthesis starting from oxazolidinone derivative of formula 11 involves number of steps. R-glyceraldehyde is converted to the required oxazolidinone derivative in four steps. R-glyceraldehyde is not very stable compound and not commercially available, although it can be prepared from the cleavage of D-mannitol-1,2,5,6-bisacetonide on treatment with lead tetraacetate or sodium periodate among other methods.

The chemoenzymatic route involves either lipase catalyzed hydrolysis or transesterification but the optical purity up to 80% was noted which needs recrystallisation of hydrochloride to improve ee to ~90%. The overall yield is moderate up to 50%.

In all the above processes cyclopropylmethyl halide has been employed for introducing cyclopropyl group as a reactive intermediate. The cyclopropylmethyl halide, is expensive, highly lachrymetric and unstable. These limitations make the reported processes economically unviable and difficult to scale up.

Therefore it is necessary to develop a short, simple, an economically viable alternative process for S-(−)-betaxolol wherein the use of cyclopropylmethyl halide is avoided, steps involving protection and deprotection are avoided and also product with improved enantiomeric purity is obtained.

OBJECTS OF INVENTION

The object of present invention is to provide a process for preparing S-(−)-betaxolol with high enantiomeric purity.

Another object is to avoid use of highly lachrymetric and unstable cyclopropylmethyl halide and also to avoid lengthier steps involving protection and deprotection of phenolic hydroxy group.

These objects are fulfilled by providing a novel S-(−)-1-{4-[2-(allyloxy)-ethyl]phenoxy}-3-isopropylamino propan-2-ol of formula 1, process for preparation thereof and use thereof in the preparation of S-(−)-betaxolol of formula 2 according to the reaction scheme given in the section titled 'Detailed description of the invention' below.

SUMMARY OF THE INVENTION

Accordingly the present invention provided S-(−)-1-{4-[2-(allyloxy)-ethyl]phenoxy}-3-isopropylamino propan-2-ol of the formula 1

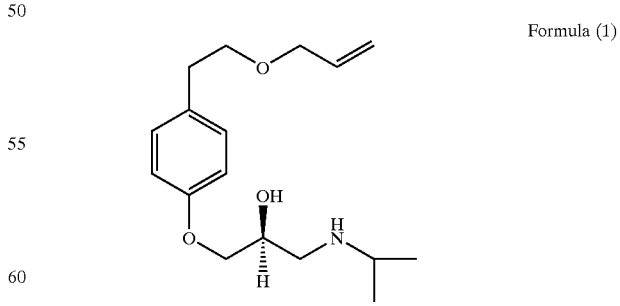

Formula (1)

or salts thereof.

The present invention also provides a process for preparation S-(−)-1-{4-[2-(allyloxy)-ethyl]phenoxy}-3-isopropylamino propan-2-ol of the formula 1

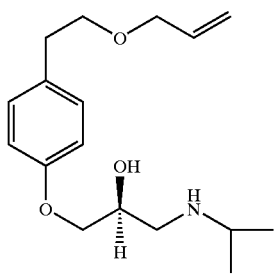

Formula (1)

or salts thereof, the process comprising:
a. selectively allylating 2-(4-hydroxyphenyl)-ethanol of formula 4 with a base and an organic solvent to give 4-(2-allyloxy-ethyl)-phenol of formula 5

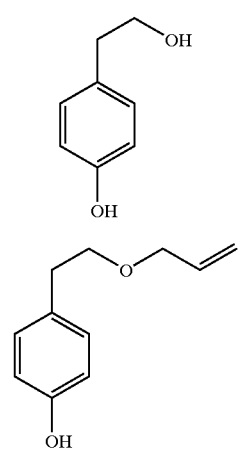

(4)

(5)

b. O-Alkylating the 4-(2-allyloxy-ethyl)-phenol of formula 5 by treating with R(−)-epichlorohydrin in the presence of an alkali to obtain a mixture of compounds of the formulae 6 and 7;

(6)

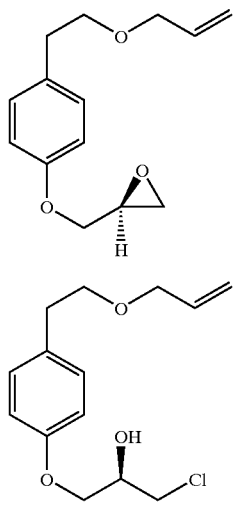

(7)

c. treating the mixture of compounds of the formulae 6 and 7 with isopropyl amine to give S-(−)-1-{4-[2-(allyloxy)-ethyl]phenoxy}-3-isopropylamino propan-2-ol of formula 1;

d. if desired, treating S-(−)-1-{4-[2-(allyloxy)-ethyl]phenoxy}-3-isopropylamino propan-2-ol of formula 1 with an acid to obtain the corresponding acid salt.

In one embodiment of the invention the base used in step (a) is selected from the group consisting of sodium hydride or potassium t-butoxide.

In another embodiment the solvent used in step (a) is an ethereal solvent such as tetrahydrofuran or a polar solvent selected from the group consisting of DMSO and DMF.

In another embodiment the alkali used in step (b) is an alkali hydroxide selected from the group consisting of sodium hydroxide or potassium hydroxide.

In another embodiment of the invention, the compound of formula 1 is reacted with hydrochloric acid to obtain a hydrochloride of formula 9

(9)

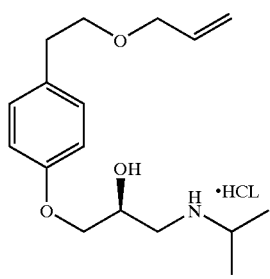

In another embodiment of the invention, the compound of formula 1 is reacted with maleic acid to obtain a maleate of formula 8

(8)

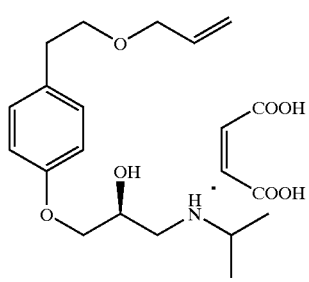

In yet another embodiment of the invention, the solvent used for preparing the hydrochloride salt of compound of formula 1 is selected from a hydrocarbons selected in turn from the group consisting of toluene and cyclohexane; a ether selected from the group consisting of diethyl ether and diisopropyl ether; and an alcohol selected from the group consisting of ethanol, methanol and isopropanol.

In another embodiment of the invention, the solvent used for preparing maleate salt of compound of formula 1 is an etheral solvent selected from the group consisting of diisopropyl ether and diethyl ether.

The present invention also relates to a process for the conversion of S-(-)-1-{4-[2-(allyloxy)-ethyl]phenoxy}-3-isopropylamino propan-2-ol of the formula 1

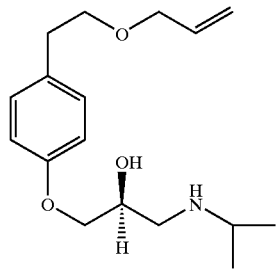

Formula (1)

to S-(-)-betaxolol of formula 2.

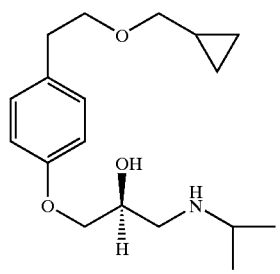

Formula (2)

or salts thereof, the process comprising cyclopropanating compound of formula 1 to obtain the chiral S-(-)-betaxolol of the formula 2, and if desired, treating the compound of formula 2 with an acid to obtain the corresponding salt.

In one embodiment of the invention, the cyclopropanation of compound of formula 1 is effected by reacting with diiodomethane using Zn—Cu couple (Simmons Smith) or diethyl zinc in hexane (Furukawa modification).

In another embodiment of the invention, the compound of formula 2 is reacted with hydrochloric acid to obtain a hydrochloride of S-(-)-betaxolol.

In another embodiment of the invention, the compound of formula 2 is reacted with maleic acid in ether to give maleate of S-(-)-betaxolol.

The solvent used for formation of hydrochloride salt of S(-) betaxolol of formula 2 is a hydrocarbon selected from the group consisting of toluene and cyclohexane or an ether selected from the group consisting of diisopropyl ether or diethyl ether, or an alcohol selected from the group consisting of ethanol, methanol and isopropanol.

DETAILED DESCRIPTION OF THE INVENTION

The present invention provides S-(-)-1-{4-[2-(allyloxy)-ethyl]phenoxy}-3-isopropylamino propan-2-ol of the formula 1, a process for preparation thereof and use thereof in preparation of S-(-)-betaxolol of formula 2. The process of preparation of compound of formula 1 comprises:

(a) selectively allylating 2-(4-hydroxyphenyl)-ethanol of formula 4 with a base and an organic solvent to give 4-(2-allyloxy-ethyl)-phenol of formula 5.

(b) O-Alkylating 4-(2-allyloxy-ethyl)-phenol of formula 5 by treating with R(-)-epichlorohydrin in the presence of alkali to obtain the mixture of compounds of the formulae 6 and 7; treating the mixture of compounds of the formulae 6 and 7 with isopropyl amine to give S-(-)-1-{4-[2-(allyloxy)-ethyl]phenoxy}-3-isopropylamino propan-2-ol of the formula 1.

(c) and if desired, treating S-(-)-1-{4-[2-(allyloxy)-ethyl]phenoxy}-3-isopropylamino propan-2-ol of the formula (1) with hydrochloric acid in IPA to give hydrochloride of formula 9 or maleic acid in ether to give maleate salt of formula 8.

The compound of formula 2 is prepared by cyclopropanating compound of formula 1 by conventional methods such as Simmon-Smith reaction or Furukawa modification to obtain the S-(-) betaxolol of formula 2. The compound of formula 2 is converted, if desired, to its acid salts by treating with hydrochloric acid in IPA to give hydrochloride of S-(-)-betaxolol or maleic acid in ether to give maleate of S-(-)-betaxolol.

The base used in step (a) may be sodium hydride or potassium t-butoxide and the solvent used is an ethereal solvent such as tetrahydrofuran or polar solvents such as DMSO or DMF. The alkali used in step (b) can be alkali hydroxides such as sodium hydroxide or potassium hydroxide. Cyclopropanation with diiodomethane of compound of formula 1 to compound of formula 2 is carried out using Zn—Cu couple (Simmons Smith) or diethyl zinc in hexane (Furukawa modification).

The solvent used for the preparation of hydrochloride salt of compound of formula 1 can be hydrocarbons such as toluene, cyclohexane, ethers such as diethyl ether, diisopropyl ether, alcohols such as ethanol, methanol and isopropanol. The solvent used for the preparation of maleate salt of compound of formula 1 can be etheral solvents such as diisopropyl ether, diethyl ether.

The solvent used for formation of hydrochloride salt of S(-) betaxolol of formula 1 may be hydrocarbons such as toluene, cyclohexane and ethers such as diisopropyl ether, diethyl ether.

SCHEME

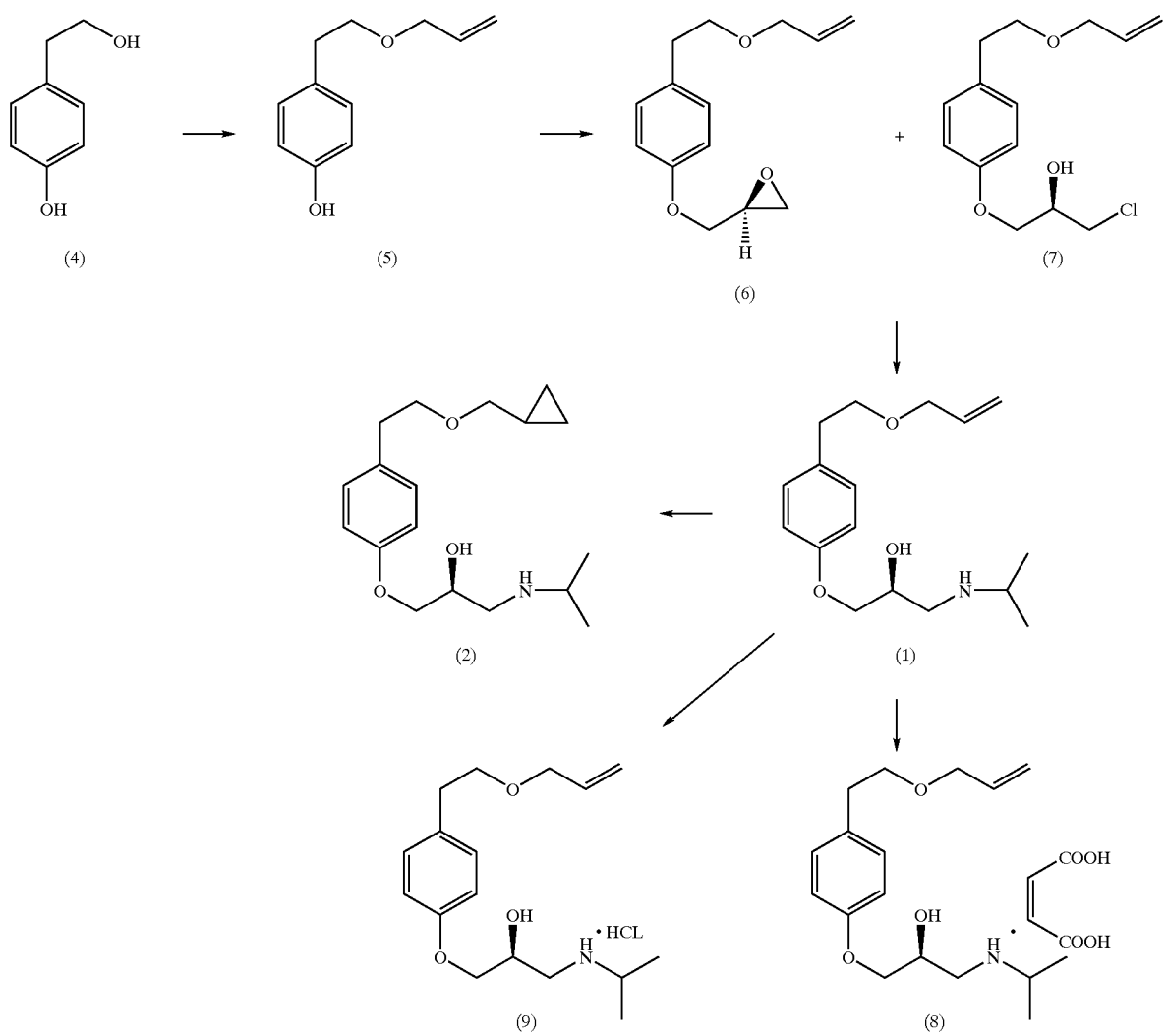

The process of the present invention is described herein below with reference to the following examples, which are illustrative and should not be construed to limit the scope of the present invention in any manner.

EXAMPLE-1

This example describes the preparation of 4-[(2-Allyloxy)-ethyl)]-phenol, of formula (5)

A reaction flask was charged with 4-hydroxy phenethyl alcohol of formula (4) (5 g, 0.036 mol), potassium tert-butoxide (12.17 g, 0.10 mol) and 20 ml of DMSO. The mixture was stirred under nitrogen at 50° C. for 30 minutes. A solution of allyl chloride (3.00 ml, 0.036 mol) was added drop wise to the reaction mixture at room temperature and further stirred for 50 min. The reaction mixture was subsequently quenched with 40 ml of water. The aqueous mixture was washed three times with 10 ml portions of toluene to remove impurities. The product was extracted from neutralized aqueous mixture with toluene. The toluene extract was then washed with water and concentrated under vacuum to afford the compound of formula (5) as an oil (3.07 g, 48%).

$^1$H NMR: 2.87 (t, 2H, CH$_2$—C); 3.64 (t, 2H, CH$_2$—O); 4.02 (d, 2H, CH$_2$—CH=CH$_2$); 5.20, 5.30 (dd, 2H, olefinic); 5.94 (m, 1H, olefinic); 6.74, 7.07 (A$_2$B$_2$, 4H, aromatic).

EXAMPLE-2

This example describes the preparation of S-(−)-1-{4-[2-(allyloxy)-ethyl]phenoxy}-3-isopropylamino propan-2-ol] of formula (5).

A solution of R-(−)-epichlorohydrin (2.58 ml, 0.028 mol) in water (1.41 ml) was stirred for 10 min. at 0–5° C. and the compound of formula (5) (3.1 g, 0.017 mol), NaOH (0.77 g, 0.019 mol) and benzyl triethyl ammonium chloride (catalytic amount) in water (18 ml) was added over a period of 1 h at 0° C. The reaction mixture was stirred for 50 h at 0° C., (monitored by TLC) and rendered acidic (pH=5) by addition of aqueous 3.5% HCl. To the reaction mixture isopropyl amine (25.74 ml, 0.435 mol) was added and stirred overnight at room temperature. The reaction mixture was concentrated and the residue extracted with chloroform and water. The organic layer was dried over sodium sulphate, concentrated on rota-vapour to afford 4.02 g (80%) as chiral compound of formula (1). ee>99 (determined by Chiral HPLC; Column-Chiracel OD 25 cm; mobile phase-hexane: isopropanol: diethyl amine (6: 4: 0.1); flow rate: 0.5 ml/min; $\lambda_{max}$:228 nm), M$^+$=293.

$^1$H NMR: 1.08, 1.09 (2 S, 6H, (CH$_3$)$_2$N); 2.69 (m, 1H, CH—CH$_3$); 2.73–2.93 (m, 7H, CH$_2$—C, CH$_2$—O,N—H, O—H, N—CH); 3.61 (t, 2H, O—CH$_2$); 3.92–4.00 (m, 4H, CH$_2$—O); 4.07 (m, 1H, CH—OH); 6.85, 7.16 (A$_2$B$_2$, 4H, aromatic).

EXAMPLE-3

This example describes the preparation of maleate salt of S-(−)-1-{4-[2-(allyloxy)-ethyl]phenoxy}-3-isopropylamino propan-2-ol of formula (8)

Compound of formula (1) (4 g, 0.014 mol) and maleic acid (1.43 g, 0.012 mol) were dissolved in ether (50 ml) and stirred for 1 hr. Filtered the white solid, which was Maleate salt of formula (8) 4.59 g (82%) mp 66° C. specific rotation: [α]$^{22}$D=−17.50 (C=2.4, MeOH).

EXAMPLE-4

This example describes the preparation of hydrochloride salt of S-(−)-1-{4-[2-(allyloxy)-ethyl]phenoxy}-3-isopropylamino propan-2-ol of formula (9)

To a solution of compound of formula (1) (2.50 g) in 15 ml of toluene, isopropanol-HCl (1 eq) (5 ml) was added drop wise under nitrogen atmosphere with stirring (untill pH=2). The reaction mixture was stirred for 1 h, concentrated and again 5 ml of toluene was added, stirring continued for 15 min. This process was repeated twice, finally solvent was removed completely and diethyl ether was added to precipitate the solid. Filtered under nitrogen atmosphere and dried to obtain the compound of formula (8) 2.42 g (86%) mp 71–73° C. specific rotation: [α]$^{22}$D=−21.77(C=2.4, MeOH).

EXAMPLE-5

This example describes the preparation of S-(−)-Betaxolol of formula (2)

To a stirred solution of compound of formula (1) (2 g, 0.007 mol) in dry toluene (15 ml), diethyl zinc (1.1 M solution in hexane, 7 ml) was added at 0° C. under nitrogen atmosphere followed by diiodomethane (4.2 ml, 0.053 mol). The reaction was stirred for 6 h at 0° C. and poured over cold aqueous solution of ammonium chloride. The organic layer was separated and the aqueous layer extracted repeatedly with diethyl ether. The combined organic layer was washed with a solution of sodium thiosulphate, dried over anhydrous sodium sulphate, filtered and concentrated to yield compound of formula (2) 1.6 g (84%). ee>99 (determined by Chiral HPLC; Column-Chiracel OD 25 cm; mobile phase-hexane: isopropanol: diethyl amine (6: 4: 0.1); flow rate: 0.5 ml/min; $\lambda_{max}$:228 nm).

$^1$H NMR: 0.20 (q, 2H, cyp); 0.53 (q, 2H, cyp); 1.07 (m, 1H, cyp); 1.08, 1.09 (2S, 6H, (CH$_3$)$_2$N); 2.69 (m, 1H, CH—CH$_3$); 2.85 (m, 4H, CH$_2$—C, CH$_2$—O); 3.27 (d, 2H, O—CH$_2$); 3.61 (t, 3H, CH—O); 3.95 (d, 2H, CH$_2$—O); 4 (m, 1H, CH—OH); 6.85, 7.16 (A$_2$B$_2$, 4H, aromatic).

Mass: M$^+$=307.

We claim:

1. S-(−)-1-{4-[2-(allyloxy)-ethyl]phenoxy}-3-isopropylamino propan-2-ol of formula 1

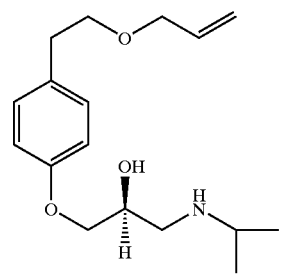

Formula (1)

or salts thereof.

2. A process for preparing S-(−)-1-{4-[2-(allyloxy)-ethyl]phenoxy}-3-isopropylamino propan-2-ol of the formula 1

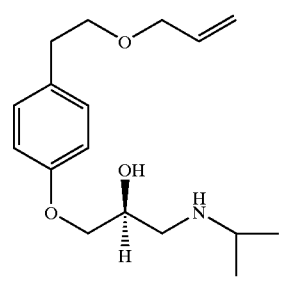

Formula (1)

or salts thereof, the process comprising:

(a) selectively allylating 2-(4-hydroxyphenyl)-ethanol of formula 4 with a base and an organic solvent to give 4-(2-allyloxy-ethyl)-phenol of formula 5

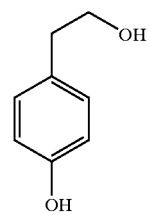

(4)

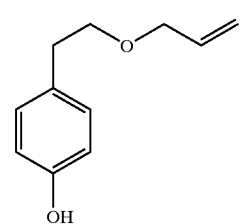

(5)

(b) O-Alkylating the 4-(2-allyloxy-ethyl)-phenol of formula 5 by treating with R(−)-epichlorohydrin in the presence of an alkali to obtain a mixture of compounds of the formulae 6 and 7;

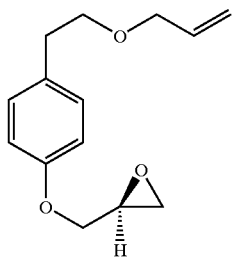
(6)

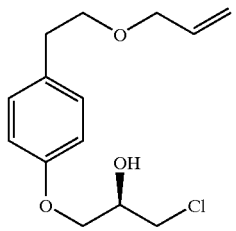
(7)

(c) treating the mixture of compounds of the formulae 6 and 7 with isopropyl amine to give S-(−)-1-{4-[2-(allyloxy)-ethyl]phenoxy}-3-isopropylamino propan-2-ol of formula 1;

(d) if desired, treating S-(−)-1-{4-[2-(allyloxy)-ethyl]phenoxy}-3-isopropylamino propan-2-ol of formula 1 with an acid to obtain the corresponding acid salt.

3. A process as claimed in claim 2 wherein the base used in step (a) is selected from the group consisting of sodium hydride or potassium t-butoxide.

4. A process as claimed in claim 2 wherein the solvent used in step (a) is an ethereal solvent comprising of tetrahydrofuran or a polar solvent selected from the group consisting of DMSO and DMF.

5. A process as claimed in claim 2 wherein the alkali used in step (b) is an alkali hydroxide selected from the group consisting of sodium hydroxide or potassium hydroxide.

6. A process as claimed in claim 2 wherein the compound of formula 1 is reacted with hydrochloric acid to obtain a hydrochloride of formula 9

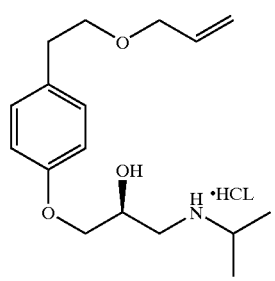
(9)

7. A process as claimed in claim 2 wherein the compound of formula 1 is reacted with maleic acid to obtain a maleate of formula 8

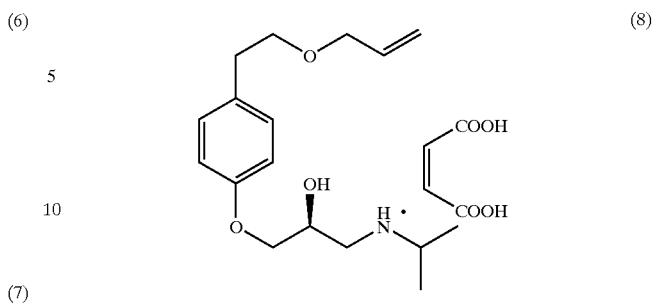
(8)

8. A process as claimed in claim 6 wherein the solvent used for preparing the hydrochloride salt of compound of formula 1 is selected from a hydrocarbons selected in turn from the group consisting of toluene and cyclohexane; a ether selected from the group consisting of diethyl ether and diisopropyl ether; and an alcohol selected from the group consisting of ethanol, methanol and isopropanol.

9. A process as claimed in claim 7 wherein the solvent used for preparing maleate salt of compound of formula 1 is an etheral solvent selected from the group consisting of diisopropyl ether and diethyl ether.

10. A process for the conversion of S-(−)-1-{4-[2-(allyloxy)-ethyl]phenoxy}-3-isopropylamino propan-2-ol of the formula 1

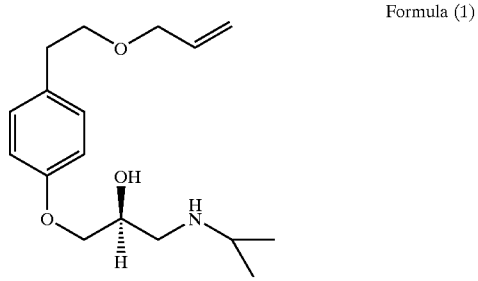
Formula (1)

to S-(−)-betaxolol of formula 2 or salts thereof,

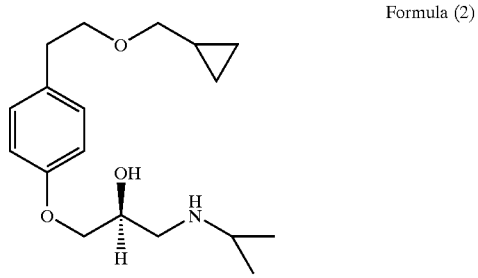
Formula (2)

the process comprising cyclopropanating compound of formula 1 to obtain the chiral S-(−)-betaxolol of the formula 2, and if desired, treating the compound of formula 2 with an acid to obtain the corresponding salt.

11. A process as claimed in claim 10 wherein the cyclopropanation of compound of formula 1 is effected by reacting with diiodomethane using Zn—Cu couple (Simmons Smith) or diethyl zinc in hexane (Furukawa modification).

12. A process as claimed in claim 10 wherein the compound of formula 2 is reacted with hydrochloric acid to obtain a hydrochloride of S-(−)-betaxolol.

13. A process as claimed in claim 10 wherein the compound of formula 2 is reacted with maleic acid in ether to give maleate of S-(−)-betaxolol.

14. A process as claimed in claim 12 wherein the solvent used for formation of hydrochloride salt of S(−) betaxolol of formula 2 is a hydrocarbon selected from the group consisting of toluene and cyclohexane or an ether selected from the group consisting of diisopropyl ether or diethyl ether, or an alcohol selected from the group consisting of ethanol, methanol and isopropanol.

* * * * *